United States Patent [19]
Grammenos et al.

[11] Patent Number: 5,998,446
[45] Date of Patent: Dec. 7, 1999

[54] 2-[2-(HETARYL OXYMETHYLENE)PHENYL] CROTONATES USED AS PESTICIDES AND FUNGICIDES

[75] Inventors: Wassilios Grammenos, Ludwigshafen; Bernd Müller, Frankenthal; Hubert Sauter, Mannheim; Klaus Oberdorf, Heidelberg; Hartmann König, Heidelberg; Norbert Götz, Worms; Michael Rack, Heidelberg; Gisela Lorenz, Hambach; Eberhard Ammermann, Heppenheim; Siegfried Strathmann, Limburgerhof, all of Germany

[73] Assignee: BASF Aktiengesellschaft, Ludwigshafen, Germany

[21] Appl. No.: 08/952,987

[22] PCT Filed: May 13, 1996

[86] PCT No.: PCT/EP96/02043

§ 371 Date: Nov. 20, 1997

§ 102(e) Date: Nov. 20, 1997

[87] PCT Pub. No.: WO96/37480

PCT Pub. Date: Nov. 28, 1996

[30] Foreign Application Priority Data

May 24, 1995 [DE] Germany ............ 195 19 040

[51] Int. Cl.⁶ ............ A01N 43/653; C07D 249/12
[52] U.S. Cl. ............ 514/340; 514/241; 514/252; 514/256; 514/363; 514/364; 514/384; 514/342; 544/189; 544/198; 544/238; 544/333; 546/268.7; 546/269.4; 546/272.4; 548/264.2; 548/264.4
[58] Field of Search ............ 546/272.4; 548/264.2; 548/264.4; 514/340, 384

[56] References Cited

U.S. PATENT DOCUMENTS

| | | | |
|---|---|---|---|
| 4,937,372 | 6/1990 | Wenderoth et al. | 560/55 |
| 5,298,527 | 3/1994 | Grammenos et al. | 514/539 |
| 5,416,068 | 5/1995 | Grammenos et al. | 504/378 |

FOREIGN PATENT DOCUMENTS 513580  11/1992  European Pat. Off. .

*Primary Examiner*—Laura L. Stockton
*Attorney, Agent, or Firm*—Keil & Weinkauf

[57] ABSTRACT

There are described compounds of the general formula I

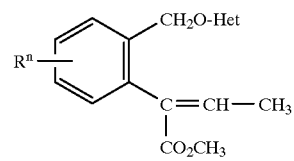

where the index and the substituents have the following meanings:

R is cyano, halogen, alkyl or alkoxy;

n is 0, 1 or 2, it being possible for the substituents R to differ from each other if n is 2;

Het is a 5-membered heteroaromatic ring having three nitrogen atoms or two nitrogen atoms and one oxygen or sulfur atom and having attached to it an unsubstituted or substituted 6-membered aromatic or heteroaromatic ring;

processes for their preparation, and their use.

7 Claims, No Drawings

2-[2-(HETARYL OXYMETHYLENE)PHENYL] CROTONATES USED AS PESTICIDES AND FUNGICIDES

This application is a 371 of PCT/EP96/02043 filed May 13, 1996.

The present invention relates to compounds of the general formula I

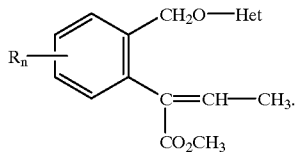

where the index and the substituents have the following meanings:

R is cyano, halogen, $C_1$–$C_4$-alkyl or $C_1$–$C_4$-alkoxy;

n is 0, 1 or 2, it being possible for the substituents R to differ from each other if n is 2;

Het is a 5-membered heteroaromatic ring having three nitrogen atoms or two nitrogen atoms and one oxygen or sulfur atom and having attached to it an unsubstituted or substituted phenyl ring or an unsubstituted or substituted 6-membered heteroaromatic ring which, in turn, has one to four nitrogen atoms.

Moreover, the invention relates to processes for the preparation of these compounds, to compositions comprising them, and to their use for controlling animal or fungal pests.

The literature discloses hetaryloxymethylenephenylcrotonates in which the heteroaromatic ring can have attached to it a phenyl group in the Het-position (EP-A 513 580).

However, it was an object of the present invention to provide compounds having improved characteristics.

Accordingly, we have found that this object is achieved by the compounds I defined at the outset. Moreover, there have been found processes for their preparation, compositions comprising them and their use for controlling animal or fungal pests.

The compounds I are prepared by a method sismilar to those described in the literature quoted at the outset by reacting a compound of the formula II with a benzyl compound of the formula III in an inert organic solvent in the presence of a base.

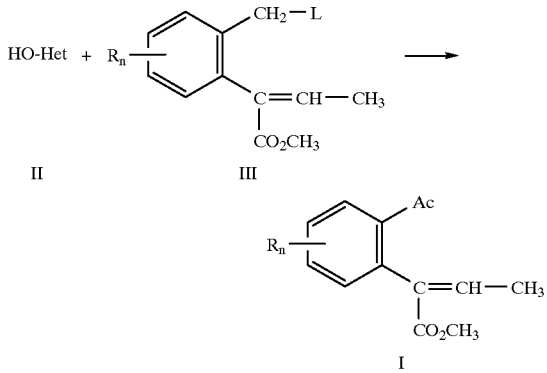

L in formula III is a nucleophilically exchangeable leaving group, such as halogen (eg. fluorine, chlorine, bromine and iodine, in particular chlorine, bromine and iodine) or a sulfonyl radical (eg. methylsulfonyl, trifluoromethylsulfonyl, phenylsulfonyl and methylphenylsulfonyl).

This reaction is conventionally carried out at from 0° C. to 120° C., preferably 20° C. to 90° C.

Suitable solvents are ethers, such as diethyl ether, diisopropyl ether, tert-butyl methyl ether, dioxane, anisole and tetrahydrofuran, nitriles, such as acetonitrile and propionitrile, ketones, such as acetone, methyl ethyl ketone, diethyl ketone and tert-butyl methyl ketone, alcohols, such as methanol, ethanol, n-propanol, isopropanol, n-butanol and tert-butanol, and also dimethyl sulfoxide and dimethylformamide, particularly preferably tetrahydrofuran, acetonitrile, acetone and dimethylformamide. Mixtures of these can also be used.

Suitable bases are, generally, inorganic compounds such as alkali metal and alkaline earth metal hydroxides, such as lithium hydroxide, sodium hydroxide, potassium hydroxide and calcium hydroxide, alkali metal and alkaline earth metal oxides, such as lithium oxide, sodium oxide, calcium oxide and magnesium oxide, alkali metal and alkaline earth metal hydrides, such as lithium hydride, sodium hydride, potassium hydride and calcium hydride, alkali metal amides, such as lithium amide, sodium amide and potassium amide, alkali metal and alkaline earth metal carbonates, such as lithium carbonate, potassium carbonate and calcium carbonate, and also alkali metal hydrogen carbonates, such as sodium hydrogen carbonate, alkali metal and alkaline earth metal alcoholates, such as sodium methanolate, sodium ethanolate, potassium ethanolate, potassium tert-butanolate and dimethoxymagnesium, furthermore organic bases, eg. tertiary amines, such as trimethylamine, triethylamine, triisopropylethylamine and N-methylpiperidine, pyridine, substituted pyridines, such as collidine, lutidine and 4-dimethylaminopyridine, and also bicyclic amines.

Sodium hydride, potassium carbonate and sodium methanolate are particularly preferred. The bases are generally employed in catalytic amounts, but they can also be used in equimolar amounts, in an excess or, if desired, as the solvent.

The educts are generally reacted with each other in equimolar amounts. It may be advantageous for the yield to employ an excess or substoichiometric amount of II based on III.

The reaction mixtures are worked in the customary manner, eg. by mixing with water, separating the phases and, if desired, purifying the crude products by chromatography. Some of the intermediates and end products are obtained in the form of colorless or pale brown, viscous oils which are freed or purified from volatile components under reduced pressure at moderately elevated temperature. If the intermediates and end products are obtained as solids, they can also be purified by recrystallization or digestion.

Those starting materials II which are required for the preparation of the compounds I are disclosed in the literature [hydroxytriazole: DE-A 24 17 970; DE-A 22 60 015; Synthesis 1987, 986; J. Med. Chem. 33, (1990) 2772; Chem. Ber. 56, (1974) 1223; DE-A 21 50 169; DE-A 22 00 436; US-A-4,433,148; hydroxyoxadiazole [sic]: J. Am. Pharm. Assoc. 67, (1958) 799; J. Org. Chem. 27, (1962) 3472; J. Heterocycl. Chem. 19, (1982) 541; Chem. Ber. 18, (1885) 2467; Chem. Ber. 18, (1885) 2456; Chem. Ber. 19, (1886) 1475; Chem. Ber. 19, (1886) 1481; Comp. Rend. 26(1), (1965) 174; DE-A 22 12 797; hydroxythiadiazoles: Monatsh. d. Chem. 113(6–7), (1982) 793; EP-A 455 356; EP-A 389 901; EP-A 307 142; DE-A 40 31 158] or can be prepared by methods described in the literature-cited.

The preparation of the compounds III is described in EP-A 513 580.

In the definitions of the symbols which are given in the abovementoned formulae, collective terms were used which generally represent the following substituents:

halogen: fluorine, chlorine, bromine and iodine;

alkyl: a saturated, straight-chain or branched hydrocarbon radical having 1 to 6 carbon atoms, eg. methyl, ethyl, propyl, 1-methylethyl, butyl, 1-methyl-propyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl;

haloalkyl: a straight-chain or branched alkyl group having 1 to 6 carbon atoms (as mentioned above), it being possible for the hydrogen atoms in this group to be fully or partially replaced by halogen atoms as mentioned above, eg. $C_1$–$C_2$-haloalkyl, such as chloromethyl, dichloromethyl, trichloromethyl, fluoromethyl, difluoromethyl, trifluoromethyl, chlorofluoromethyl, dichlorofluoromethyl, chlorodifluoromethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl and pentafluoroethyl;

alkoxy: a straight-chain or branched alkyl group having 1 to 6 carbon atoms (as mentioned above), which is bonded to the skeleton via an oxygen atom (—O—);

haloalkoxy: a straight-chain or branched haloalkyl group having 1 to 6 carbon atoms (as mentioned above), which is bonded to the skeleton via an oxygen atom (—O—);

alkylamino: a straight-chain or branched alkyl group having 1 to 6 carbon atoms (as mentioned above), which is bonded to the skeleton via an amino group (—NH—);

dialkylamino: an amino group which has attached to it two straight-chain or branched alkyl groups which are independent of each other and have in each case 1 to 6 carbon atoms (as mentioned above);

alkoxycarbonyl: a straight-chain or branched alkyl group having 1 to 6 carbon atoms (as mentioned above), which is bonded to the skeleton via an oxycarbonyl group (—O—CO—);

5-membered heteroaromatic ring: a 5-membered heteroaromatic ring having three nitrogen atoms as ring members, or a 5-membered heteroaromatic ring having two nitrogen atoms and one oxygen or sulfur atom as ring members, eg. triazole, oxadiazole and thiadiazole;

6-membered heteroaromatic ring: a 6-membered heteroaromatic ring having one to four nitrogen atoms as ring members, eg. pyridine, pyridazine, pyrimidine, pyrazine, triazine and tetrazine.

Particularly preferred compounds I are those where n is 0 or 1.

Other particularly preferred compounds I are those where n is 1 and R is cyano, fluorine, chlorine, methyl or methoxy.

Equally particularly preferred compounds I are those where Het is a group of the formulae II.1 to II.5:

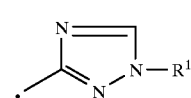

II.1

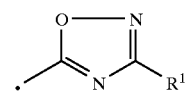

II.2

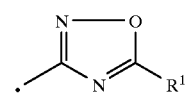

II.3

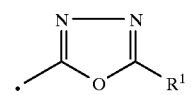

II.4

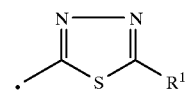

II.5

Particularly preferred compounds I are those where $R^1$ is unsubstituted or substituted phenyl.

Equally particularly preferred compounds I are those where $R^1$ is phenyl which can be partially or fully halogenated and/or can have attached to it one to five of the following radicals: $C_1$–$C_4$-alkyl, $C_1$–$C_4$-haloalkyl, $C_1$–$C_4$-alkyloxy, $C_1$–$C_4$-haloalkyloxy, $C_1$–$C_4$-alkylamino, di-$C_1$–$C_4$-alkylamino and $C_1$–$C_4$-alkoxycarbonyl.

Particularly preferred compounds I are those where Het has attached to it one of the following radicals: unsubstituted or substituted pyridine, pyrimidine, pyrazine and triazine.

Other particularly preferred compounds I are those where the 6-membered heteroaromatic ring on Het is partially or fully halogenated and/or has attached to it one to three of the following radicals: $C_1$–$C_4$-alkyl, $C_1$–$C_4$-haloalkyl, $C_1$–$C_4$-alkoxy, $C_1$–$C_4$-haloalkoxy, $C_1$–$C_4$-alkylamino, di-$C_1$–$C_4$-alkylamino and $C_1$–$C_4$-alkoxycarbonyl.

Particularly preferred compounds I are those where the 6-membered heteroaromatic ring on Het can have attached to it one to three of the following radicals: fluorine, chlorine, bromine, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylamino, di-$C_1$–$C_4$-alkylamino and $C_1$–$C_4$-alkoxycarbonyl.

Particularly preferred with regard to their use are the compounds I which are compiled in the tables which follow. In the tables, the groups mentioned for a substituent furthermore represent, on their own (independently of the combination in which they are mentioned), a particularly preferred embodiment of the substituent in question.

TABLE 1

Compounds of the general formula I.A, where n is 0 and $R^1$ corresponds for any one compound to one line of Table A

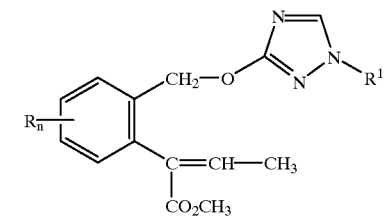

I.A

TABLE 2

Compounds of the general formula I.B, where n is 0 and $R^1$ corresponds for any one compound to one line of Table A

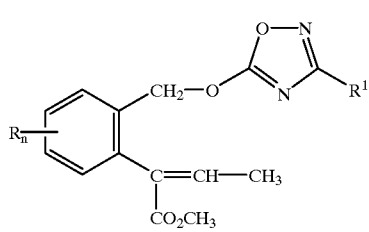

I.B

TABLE 3

Compounds of the general formula I.C, where n is 0 and $R^1$ corresponds for any one compound to one line of Table A

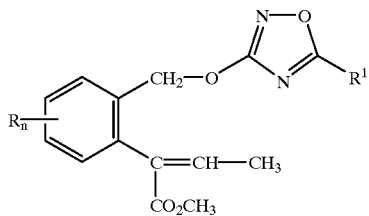

I.C

TABLE 4

Compounds of the general formula I.D, where n is 0 and $R^1$ corresponds for any one compound to one line of Table A

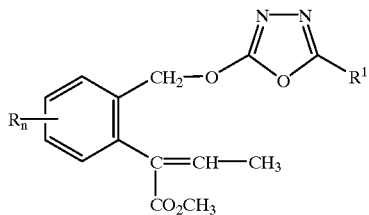

I.D

TABLE 5

Compounds of the general formula I.E, where n is 0 and $R^1$ corresponds for any one compound to one line of Table A

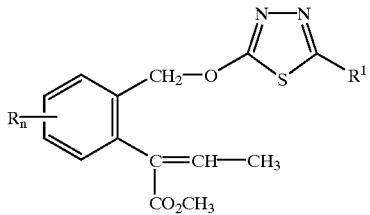

I.E

TABLE A

| $R^1$ | $R^1$ | $R^1$ |
|---|---|---|
| $C_6H_5$ | 2-$CH_3$—$C_6H_4$ | 2-F, 4-$CH_3$—$C_6H_3$ |
| 2-Cl—$C_6H_4$ | 3-$CH_3$—$C_6H_4$ | 4-F, 2-$CH_3$—$C_6H_3$ |
| 3-Cl—$C_6H_4$ | 4-$CH_3$—$C_6H_4$ | 5-Cl, 2-$CH_3$—$C_6H_3$ |
| 4-Cl—$C_6H_4$ | 2,3-$(CH_3)_2$—$C_6H_3$ | 4-$C_2H_5$—$C_6H_4$ |
| 2-F—$C_6H_4$ | 2,4-$(CH_3)_2$—$C_6H_3$ | 4-$CH(CH_3)_2$—$C_6H_4$ |
| 3-F—$C_6H_4$ | 2,5-$(CH_3)_2$—$C_6H_3$ | 4-$C(CH_3)_3$—$C_6H_4$ |
| 4-F—$C_6H_4$ | 2,6-$(CH_3)_2$—$C_6H_3$ | 4-$OC_2H_5$—$C_6H_4$ |
| 2-Br—$C_6H_4$ | 3,4-$(CH_3)_2$—$C_6H_3$ | 4-$OCH(CH_3)_2$—$C_6H_4$ |
| 3-Br—$C_6H_4$ | 3,5-$(CH_3)_2$—$C_6H_3$ | 4-$OC(CH_3)_3$—$C_6H_4$ |
| 4-Br—$C_6H_4$ | 2-$CF_3$—$C_6H_4$ | pyridin-2-yl |
| 2,3-$Cl_2$—$C_6H_3$ | 3-$CF_3$—$C_6H_4$ | pyridin-3-yl |
| 2,4-$Cl_2$—$C_6H_3$ | 4-$CF_3$—$C_6H_4$ | pyridin-4-yl |
| 2,5-$Cl_2$—$C_6H_3$ | 2,3-$(CF_3)_2$—$C_6H_3$ | 6-Cl-pyridin-2-yl |
| 2,6-$Cl_2$—$C_6H_3$ | 2,4-$(CF_3)_2$—$C_6H_3$ | 5-Cl-pyridin-2-yl |
| 3,4-$Cl_2$—$C_6H_3$ | 2,5-$(CF_3)_2$—$C_6H_3$ | 6-$CH_3$-pyridin-2-yl |
| 3,5-$Cl_2$—$C_6H_3$ | 2,6-$(CF_3)_2$—$C_6H_3$ | 5-$CH_3$-pyridin-2-yl |
| 2,3-$F_2$—$C_6H_3$ | 3,4-$(CF_3)_2$—$C_6H_3$ | 6-$C_2H_5$-pyridin-2-yl |
| 2,4-$F_2$—$C_6H_3$ | 3,5-$(CF_3)_2$—$C_6H_3$ | 6-$CH(CH_3)_2$-pyridin-2-yl |
| 2,5-$F_2$—$C_6H_3$ | 2-$OCH_3$—$C_6H_4$ | 6-$C(CH_3)_3$-pyridin-2-yl |
| 2,6-$F_2$—$C_6H_3$ | 3-$OCH_3$—$C_6H_4$ | 6-$CF_3$-pyridin-2-yl |
| 3,4-$F_2$—$C_6H_3$ | 4-$OCH_3$—$C_6H_4$ | 5-$CF_3$-pyridin-2-yl |
| 3,5-$F_2$—$C_6H_3$ | 2,3-$(OCH_3)_2$—$C_6H_3$ | 4-$CH_3$-pyridin-2-yl |
| 2,3-$Br_2$—$C_6H_3$ | 2,4-$(OCH_3)_2$—$C_6H_3$ | 6-F-pyridin-2-yl |
| 2,4-$Br_2$—$C_6H_3$ | 2,5-$(OCH_3)_2$—$C_6H_3$ | 5-F-pyridin-2-yl |
| 2,5-$Br_2$—$C_6H_3$ | 2,6-$(OCH_3)_2$—$C_6H_3$ | 4-F-pyridin-2-yl |
| 2,6-$Br_2$—$C_6H_3$ | 3,4-$(OCH_3)_2$—$C_6H_3$ | pyrimidin-2-yl |
| 3,4-$Br_2$—$C_6H_3$ | 3,5-$(OCH_3)_2$—$C_6H_3$ | pyrimidin-4-yl |
| 3,5-$Br_2$—$C_6H_3$ | 2,3,5-$(CH_3)_3$—$C_6H_2$ | pyrimidin-5-yl |
| 2,3,5-$Cl_3$—$C_6H_2$ | 2,3,5-$(CF_3)_3$—$C_6H_2$ | 4-$CH_3$-pyrimidin-2-yl |
| 2,3,5-$Br_3$—$C_6H_2$ | 2,3,5-$(OCH_3)_3$—$C_6H_2$ | 4,6-$(CH_3)_2$-pyrimidin-2-yl |
| 2,3,5-$F_3$—$C_6H_2$ | 2-F, 5—$CH_3$—$C_6H_3$ | 4,6-$(OCH_3)_2$-pyrimidin-2-yl |
| 2-F, 4-Cl—$C_6H_3$ | 5-F, 2-$CH_3$—$C_6H_3$ | 6-$CH_3$-pyrimidin-4-yl |
| 4-F, 2-Cl—$C_6H_3$ | 2-Cl, 4-$CH_3$—$C_6H_3$ | pyridazin-2-yl |
| 4-Cl, 2-$CH_3$—$C_6H_3$ | 2-Cl, 5-$CH_3$—$C_6H_3$ | triazin-2-yl |

The compounds I are useful as fungicides.

The compounds I are distinguished by an outstanding activity against a broad spectrum of phytopathogenic fungi, in particular from the classes of the Ascomycetes and Basidiomycetes. Some of them are systemically active and can be used as foliar—and soil-acting fungicides.

They are particularly important for controlling a large number of fungi on a variety of crop plants, such as wheat, rye, barley, oats, rice, maize, grass, cotton, soya, coffee, sugar cane, grape vine, fruit crops, ornamentals, and vegetables such as cucumbers, beans and cucurbits, and on the seeds of these plants.

Specifically, they are suitable for controlling the following plant diseases: Erysiphe graminis (powdery mildew) in cereals, *Erysiphe cichoracearum* and *Sphaerotheca fuliginea* on cucurbits, *Podosphaera leucotricha* on apples, *Uncinula necator* on grape vine, *Puccinia species* on cereals, Rhizoctonia species on cotton and in lawns, Ustilago species on cereals and sugar cane, *Venturia inaequalis*

(scab) on apples, Helminthosporium species on cereals, *Septoria nodorum* on wheat, *Botrytis cinerea* (gray mold) on strawberries, grape vine, *Cercospora arachidicola* on groundnuts, *Pseudocercosporella herpotrichoides* on wheat, barley, *Pyricularia oryzae* on rice, *Phytophthora infestans* on potatoes and tomatoes, Fusarium and Verticillium species on a variety of plants, *Plasmopara viticola* on grape vine and Alternaria species on vegetables and fruit.

The compounds I are used by treating the fungi or the plants, seed, materials or the soil to be protected against fungal infection with a fungicidally active amount of the active ingredients. Application is effected before or after infection of the materials, plants or seeds by the fungi.

They can be converted into the customary formulations, such as solutions, emulsions, suspensions, dusts, powders, pastes and granules. The use form depends on the intended purpose; in any case, it should guarantee fine and uniform distribution of the ortho-substituted benzyl ester of a cyclopropanecarboxylic acid. The formulations are prepared in a known manner, eg. by extending the active ingredient with solvents and/or carriers, if desired using emulsifiers and dispersants, it also being possible to use other organic solvents as auxiliary solvents if water is used as the diluent. Suitable auxiliaries are essentially: solvents such as aromatics (eg. xylene), chlorinated aromatics (eg. chlorobenzenes), paraffins (eg. mineral oil fractions), alcohols (eg. methanol, butanol), ketones (eg. cyclohexanone), amines (eg. ethanolamine, dimethylformamide) and water; carriers such as ground natural minerals (eg. kaolins, clays, talc, chalk) and ground synthetic minerals (eg. highly-disperse silica, silicates); emulsifiers such as non-ionic and anionic emulsifiers (eg. polyoxyethylene fatty alcohol ethers, alkylsulfonates and arylsulfonates) and dispersants, such as lignosulfite waste liquors and methylcellulose.

In general, the fungicidal compositions comprise from 0.1 to 95, preferably 0.5 to 90, % by weight of active ingredient.

Depending on the nature of the desired effect, the rates of application are from 0.01 to 2.0 kg of active ingredient per ha.

In the treatment of seed, amounts of from 0.001 to 0.1 g, preferably 0.01 to 0.05 g, of active ingredient are generally required per kilogram of seed.

In the use form as fungicides, the compositions according to the invention may also be present-together with other active ingredients, the eg. with herbicides, insecticides, growth regulators, fungicides or else with fertilizers.

A mixture with fungicides frequently results in a widened fungicidal spectrum of action.

The following list of fungicides together with which the compounds according to the invention can be used is intended to illustrate the possible combinations, but not to impose any limitation:

sulfur, dithiocarbamates and their derivatives, such as iron(III) dimethyldithiocarbamate, zinc dimethyldithiocarbamate, zinc ethylenebisdithiocarbamate, manganese ethylenebisdithiocarbamate, anganese zinc ethylenediamine-bis-dithiocarbamate, tetramethylthiuram disulfides, ammonia complex of zinc (N,N-ethylene-bis-dithiocarbamate), ammonia complex of zinc (N,N'-propylene-bis-dithiocarbamate), zinc (N,N'-propylenebisdithiocarbamate), N,N'-polypropylenebis(thiocarbamoyl)disulfide;

nitro derivatives, such as dinitro(l-methylheptyl)phenyl crotonate, 2-sec-butyl-4,6-dinitrophenyl-3,3-dimethyl acrylate, 2-sec-butyl-4,6-dinitrophenylisopropyl carbonate, di-isopropyl 5-nitroisophthalate;

heterocyclic substances, such as 2-heptadecyl-2-imidazoline acetate, 2,4-dichloro-6-(o-chloroanilino)-s-triazine, O,O-diethyl phthalimidophosphonothioate, 5-amino-1-[bis-(dimethylamino)-phosphinyl]-3-phenyl-1,2,4-triazole, 2,3-dicyano-1,4-dithioanthraquinone, 2-thio-1,3-dithiolo[4,5-b]quinoxaline, methyl 1-(butylcarbamoyl)-2-benzimidazolecarbamate, 2-methoxycarbonylaminobenzimidazole, 2-(furyl-(2))benzimidazole, 2-(thiazolyl-(4))benzimidazole, N-(1,1,2,2-tetrachloroethylthio)tetrahydrophthalimide, N-trichloromethylthiotetrahydrophthalimide, N-trichloromethylthiophthalimide, N-dichlorofluoromethylthio-N',N'-dimethyl-N-phenylsulfuric diamide, 5-ethoxy-3-trichloromethyl-1,2,3-thiadiazole, 2-thiocyanomethylthiobenzothiazole, 1,4-dichloro-2,5-dimethoxybenzene, 4-(2-chlorophenylhydrazono)-3-methyl-5-isoxazolone, pyridine 2-thio-1-oxide, 8-hydroxyquinoline or its copper salt, 2,3-dihydro-5-carboxanilido-6-methyl-1,4-oxathiine, 2,3-dihydro-5-carboxanilido-6-methyl-1,4-oxathiine 4,4-dioxide, 2-methyl-5,6-dihydro-4H-pyran-3-carboxanilide, 2-methylfuran-3-carboxanilide, 2,5-dimethylfuran-3-carboxanilide, 2,4,5-trimethylfuran-3-carboxanilide, N-cyclohexyl-2,5-dimethylfuran-3-carboxamide, N-cyclohexyl-N-methoxy-2,5-dimethylfuran-3-carboxamide, 2-methylbenzanilide, 2-iodobenzanilide, N-formyl-N-morpholine 2,2,2-trichloroethyl acetal, piperazine-1,4-diylbis(1-(2,2,2-trichloroethyl)formamide [sic], 1-(3,4-dichloroanilino)-1-formylamino-2,2,2-trichloroethane, 2,6-dimethyl-N-tridecyl-morpholine or its salts, 2,6-dimethyl-N-cyclododecylmorpholine or its salts, N-[3-(p-tert-butylphenyl)-2-methylpropyl]-cis-2,6-dimethyl-morpholine, N-[3-(p-tert-butylphenyl)-2-methylpropyl]piperidine, 1-[2-(2,4-dichlorophenyl)-4-ethyl-1,3-dioxolan-2-yl-ethyl]-1H-1,2,4-triazole, 1-[2-(2,4-dichlorophenyl)-4-n-propyl-1,3-dioxolan-2-yl-ethyl]-1H-1,2,4-triazole, N-(n-propyl)-N-(2,4,6-trichlorophenoxyethyl)-N'-imidazolylurea, 1-(4-chlorophenoxy)-3,3-dimethyl-1-(1H-1,2,4-triazol-1-yl)-2-butanone, 1-(4-chlorophenoxy)-3,3-dimethyl-1-(1H-1,2,4-triazol-1-yl)-2-butanol, α-(2-chlorophenyl)-α-(4-chlorophenyl)-5-pyrimidinemethanol, 5-butyl-2-dimethylamino-4-hydroxy-6-methylpyrimidine, bis(p-chlorophenyl)-3-pyridinemethanol, 1,2-bis(3-ethoxycarbonyl-2-thioureido)benzene, 1,2-bis(3-methoxycarbonyl-2-thioureido)benzene, and a variety of fungicides, such as dodecylguanidine acetate, 3-[3-(3,5-dimethyl-2-oxycyclohexyl)-2-hydroxyethyl]glutarimide, hexachlorobenzene, methyl N-(2,6-dimethylphenyl)-N-(2-furoyl)-DL-alaninate, DL-N-(2,6-dimethyl-phenyl)-N-(2'-methoxyacetyl)-alanine methyl ester, N-(2,6-dimethylphenyl)-N-chloroacetylD,L-2-aminobutyrolactone, DL-N-(2,6-dimethylphenyl)-N-(phenylacetyl)alanine methyl ester, 5-methyl-5-vinyl-3-(3,5-dichlorophenyl)-2,4-dioxo-1,3-oxazolidine, 3-[3,5-dichlorophenyl(-5-methyl-5-methoxymethyl]-1,3-oxazolidine-2,4-dione [sic], 3-(3,5-dichlorophenyl)-1-isopropylcarbamoylhydantoin, N-(3,5-dichlorophenyl)-1,2-dimethylcyclopropane-1,2-dicarboximide, 2-cyano-[N-(ethylaminocarbonyl)-2-methoximino]acetamide, 1-[2-(2,4-dichlorophenyl)-pentyl]-1H-1,2,4-triazole, 2,4-difluoro-a-(1H-1,2,4-triazolyl-1-methyl)-benzhydryl alcohol, N-(3-chloro-2,6-dinitro-4-trifluoromethylphenyl)-5-trifluoromethyl-3-chloro-2-aminopyridine, 1-((bis(4-fluorophenyl)methylsilyl)methyl)-1H-1,2,4-triazole.

The compounds of the formula I are furthermore suitable for effectively controlling animal pests from the classes of the insects, arachnids and nematodes. They can be employed as pesticides in crop protection and in the hygiene, stored-product and veterinary sector.

The insect pests include, from the order of the lepidopterans (Lepidoptera), for example, *Agrotis ypsilon, Agrotis segetum, Alabama argillacea, Anticarsia gemmatalis, Argyresthia conjugella, Autographa gamma, Bupalus piniarius, Cacoecia murinana, Capua reticulana, Cheimatobia brumata, Choristoneura fumiferana, Choristoneura occidentalis, Cirphis unipuncta, Cydia pomonella, Dendrolimus pini, Diaphania nitidalis, Diatraea grandiosella, Earias insulana, Elasmopalpus lignosellus, Eupoecilia ambiguella, Evetria bouliana, Feltia subterranea, Galleria mellonella, Grapholitha funebrana, Grapholitha molesta, Heliothis armigera, Heliothis virescens, Heliothis zea, Hellula undalis, Hibernia defoliaria, Hyphantria cunea, Hyponomeuta malinellus, Keiferia lycopersicella, Lambdina fiscellaria, Laphygma exigua, Leucoptera coffeella, Leucoptera scitella, Lithocolletis blancardella, Lobesia botrana, Loxostege sticticalis, Lymantria dispar, Lymantria monacha, Lyonetia clerkella, Malacosoma neustria, Mamestra brassicae, Orgyia pseudotsugata, Ostrinia nubilalis, Panolis flammea, Pectinophora gossypiella, Peridroma saucia, Phalera bucephala, Phthorimaea operculella, Phyllocnistis citrella, Pieris brassicae, Plathypena scabra, Plutella xylostella, Pseudoplusia includens, Rhyacionia frustrana, Scrobipalpula absoluta, Sitotroga cerealella, Sparganothis pilleriana, Spodoptera frugiperda, Spodoptera littoralis, Spodoptera litura, Thaumatopoea pityocampa, Tortrix viridana, Trichoplusia ni, Zeiraphera canadensis.*

From the order of the beetles (Coleoptera), for example, *Agrilus sinuatus, Agriotes lineatus, Agriotes obscurus, Amphimallus solstitialis, Anisandrus dispar, Anthonomus grandis, Anthonomus pomorum, Atomaria linearis, Blastophagus piniperda, Blitophaga undata, Bruchus rufimanus, Bruchus pisorum, Bruchus lentis, Byctiscus betulae, Cassida nebulosa, Cerotoma trifurcata, Ceuthorrhynchus assimilis, Ceuthorrhynchus napi, Chaetocnema tibialis, Conoderus vespertinus, Crioceris asparagi, Diabrotica longicornis, Diabrotica 12-punctata, Diabrotica virgifera, Epilachna varivestis, Epitrix hirtipennis, Eutinobothrus brasiliensis, Hylobius abietis, Hypera brunneipennis, Hypera postica, Ips typographus, Lema bilineata, Lema melanopus, Leptinotarsa decemlineata, Limonius californicus, Lissorhoptrus oryzophilus, Melanotus communis, Meligethes aeneus, Melolontha hippocastani, Melolontha melolontha, Oulema oryzae, Ortiorrhynchus* [sic] *sulcatus, Otiorrhynchus ovatus, Phaedon cochleariae, Phyllotreta chrysocephala, Phyllophaga sp., Phyllopertha horticola, Phyllotreta nemorum, Phyllotreta striolata, Popillia japonica, Sitona lineatus, Sitophilus granaria.*

From the order of the dipterans (Diptera), for example, *Aedes aegypti, Aedes vexans, Anastrepha ludens, Anopheles maculipennis, Ceratitis capitata, Chrysomya bezziana, Chrysomya hominivorax, Chrysomya macellaria, Contarinia sorghicola, Cordylobia anthropophaga, Culex pipiens, Dacus cucurbitae, Dacus oleae, Dasineura brassicae, Fannia canicularis, Gasterophilus intestinalis, Glossina morsitans, Haematobia irritans, Haplodiplosis equestris, Hylemyia platura, Hypoderma lineata, Liriomyza sativae, Liriomyza trifolii, Lucilia caprina* [sic]*, Lucilia cuprina, Lucilia sericata, Lycoria pectoralis, Mayetiola destructor, Musca domestica, Muscina stabulans, Oestrus ovis, Oscinella frit, Pegomya hysocyami, Phorbia antiqua, Phorbia brassicae, Phorbia coarctata, Rhagoletis cerasi, Rhagoletis pomonella, Tabanus bovinus, Tipula oleracea, Tipula paludosa.*

From the order of the thrips (Thysanoptera), for example, *Frankliniella fusca, Frankliniella occidentalis, Frankliniella tritici, Scirtothrips citri, Thrips oryzae, Thrips palmi, Thrips tabaci.*

From the order of the hymenopterans (Hymenoptera), for example, *Athalia rosae, Atta cephalotes, Atta sexdens, Atta texana, Hoplocampa minuta, Hoplocampa testudinea, Monomorium pharaonis, Solenopsis geminata, Solenopsis invicta.*

From the order of the heteropterans (Heteroptera), for example, *Acrosternum hilare, Blissus leucopterus, Cyrtopeltis notatus, Dysdercus cingulatus, Dysdercus intermedius, Eurygaster integriceps, Euschistus impictiventris, Leptoglossus phyllopus, Lygus lineolaris, Lygus pratensis, Nezara viridula, Piesma quadrata, Solubea insularis, Thyanta perditor.*

From the order of the homopterans (Homoptera), for example, *Acyrthosiphon onobrychis, Adelges laricis, Aphidula nasturtii, Aphis fabae, Aphis pomi, Aphis sambuci, Brachycaudus cardui, Brevicoryne brassicae, Cerosipha gossypii, Dreyfusia nordmannianae, Dreyfusia piceae, Dysaphis radicola, Dysaulacorthum pseudosolani, Empoasca fabae, Macrosiphum avenae, Macrosiphum euphorbiae, Macrosiphon rosae, Megoura viciae, Metopolophium dirhodum, Myzodes persicae, Myzus cerasi, Nilaparvata lugens, Pemphigus. bursarius, Perkinsiella saccharicida, Phorodon humuli, Psylla mali, Psylla piri, Rhopalomyzus ascalonicus, Rhopalosiphum maidis, Sappaphis mala, Sappaphis mali, Schizaphis graminum, Schizoneura lanuginosa, Trialeurodes vaporariorum, Viteus vitifolii.*

From the order of the termites (Isoptera), for example, *Calotermes flavicollis, Leucotermes flavipes, Reticulitermes lucifugus, Termes natalensis.*

From the order of the orthopterans (Orthoptera), for example, *Acheta domestica, Blatta orientalis, Blattella germanica, Forficula auricularia, Gryllotalpa gryllotalpa, Locusta migratoria, Melanoplus bivittatus, Melanoplus femur-rubrum, Melanoplus mexicanus, Melanoplus sanguinipes, Melanoplus spretus, Nomadacris septemfasciata, Periplaneta americana, Schistocerca americana, Schistocerca peregrina, Stauronotus maroccanus, Tachycines asynamorus.*

From the class of the arachnoidea, for example, arachnids (Acarina), such as *Amblyomma americanum, Amblyomma variegatum, Argas persicus, Boophilus annulatus, Boophilus decoloratus, Boophilus microplus, Brevipalpus phoenicis, Bryobia praetiosa, Dermacentor silvarum, Eotetranychus carpini, Eriophyes sheldoni, Hyalomma truncatum, Ixodes ricinus, Ixodes rubicundus, Ornithodorus moubata, Otobius megnini, Paratetranychus pilosus, Dermanyssus gallinae, Phyllocoptruta oleivora, Polyphagotarsonemus latus, Psoroptes ovis, Rhipicephalus appendiculatus, Rhipicephalus evertsi, Sarcoptes scabiei, Tetranychus cinnabarinus, Tetranychus kanzawai, Tetranychus pacificus, Tetranychus telarius, Tetranychus urticae.*

From the class of the nematodes, for example, root knot nematodes, eg. *Meloidogyne hapla, Meloidogyne incognita, Meloidogyne javanica,* cyst nematodes, eg. *Globodera rostochiensis, Heterodera avenae, Heterodera glycines, Heterodera schachtii, Heterodera trifolii,* stem eel worms and foliar eel worms, eg. *Belonolaimus longicaudatus, Ditylenchus destructor, Ditylenchus dipsaci, Heliocotylenchus multicinctus, Longidorus elongatus, Radopholus similis,*

*Rotylenchus robustus, Trichodorus primitivus, Tylenchorhynchus claytoni, Tylenchorhynchus dubius, Pratylenchus neglectus, Pratylenchus penetrans, Pratylenchus curvitatus, Pratylenchus goodeyi.*

The active ingredients can be used as such, in the form of their formulations or in the form of the use forms prepared therefrom, eg. in the form of ready-to-spray solutions, powders, suspensions or dispersions, emulsions, oil dispersions, pastes, dusts, materials for spreading or granules by means of spraying, atomizing, dusting, spreading or pouring. The use forms depend entirely on the intended aims; in any case, they should guarantee the finest possible distribution of the active ingredients according to the invention.

The concentrations of active ingredients in the ready-to-use preparations can be varied within substantial ranges.

They are generally from 0.0001 to 10%, preferably from 0.01 to 1%.

The active ingredients can also be used successfully by the ultra-low-volume method (ULV), it being possible to apply formulations comprising more than 95% by weight of active ingredient, or even the active ingredient itself without additives.

The rate of active ingredient for controlling animal pests is from 0.1 to 2.0, preferably from 0.2 to 1.0, kg/ha, under open conditions.

Suitable substances for the preparation of ready-to-spray solutions, emulsions, pastes or oil dispersions are mineral oil fractions of medium to high boiling point, such as kerosene or diesel oil, furthermore coal tar oils and oils of vegetable or animal origin, aliphatic, cyclic and aromatic hydrocarbons, eg. benzene, toluene, xylene, paraffin, tetrahydronaphthalene, alkylated naphthalenes or their derivatives, methanol, ethanol, propanol, butanol, chloroform, carbon tetrachloride, cyclohexanol, cyclohexanone, chlorobenzene, isophorone, strongly polar solvents, eg. dimethylformamide, dimethyl sulfoxide, N-methylpyrrolidone and water.

Aqueous use forms can be prepared from emulsion concentrates, pastes or wettable powders (spraying powders, oil dispersions) by adding water. To prepare emulsions, pastes or oil dispersions, the substances can be homogenized in water by means of wetting agents, tackifiers, dispersants or emulsifiers, either as such or dissolved in an oil or solvent. Alternatively, concentrates which are suitable for dilution with water can also be prepared which are composed of active ingredient, wetting agent, tackifier, dispersant or emulsifier and, if desired, solvent or oil.

Suitable surface-active substances are alkali metal, alkaline earth metal or ammonium salts of lignosulfonic acid, naphthalenesulfonic acid, phenolsulfonic acid, dibutylnaphthalenesulfonic acid, alkylarylsulfonates, alkyl sulfates, alkylsulfonates, fatty alcohol sulfates and fatty acids and their alkali metal and alkaline earth metal salts, salts of sulfated fatty alcohol glycol ether, condensates of sulfonated naphthalene and naphthalene derivatives with formaldehyde, condensates of naphthalene or of naphthalenesulfonic acid with phenol and formaldehyde, polyoxyethylene octylphenol ether, ethoxylated isooctylphenol, octylphenol, nonylphenol, alkylphenol [sic] polyglycol ethers, tributylphenyl polyglycol ether, alkylaryl polyether alcohols, isotridecyl alcohol, fatty alcohol/ethylene oxide condensates, ethoxylated castor oil, polyoxyethylene alkyl ethers, ethoxylated polyoxypropylene, lauryl alcohol polyglycol ether acetal, sorbitol esters, lignosulfite waste liquors and methylcellulose.

Powders, materials for spreading and dusts can be prepared by mixing or jointly grinding the active ingredients with a solid carrier.

In general, the formulations comprise from 0.01 to 95% by weight, preferably from 0.1 to 90% by weight, of the active ingredient. The active ingredients are employed in a purity of from 90% to 100%, preferably from 95% to 100% (according to NMR spectrum).

Examples of formulations are:

I. 5 parts by weight of a compound according to the invention are mixed intimately with 95 parts by weight of finely divided kaolin. This gives a dust which comprises 5% by weight of the active ingredient.

II. 30 parts by weight of a compound according to the invention are mixed intimately with a mixture of 92 parts by weight of pulverulent silica gel and 8 parts by weight of paraffin oil which has been sprayed onto the surface of this silica gel. This gives a preparation of the active ingredient which has good adhesive properties (active ingredient content 23% by weight).

III. 10 parts by weight of a compound according to the invention are dissolved in a mixture composed of 90 parts by weight of xylene, 6 parts by weight of the adduct of 8 to 10 mol of ethylene oxide to 1 mol of oleic acid N-monoethanolamide, 2 parts by weight of calcium dodecylbenzenesulfonate and 2 parts by weight of the adduct of 40 mol of ethylene oxide to 1 mol of castor oil (active ingredient content 9% by weight).

IV. 20 parts by weight of a compound according to the invention are dissolved in a mixture composed of 60 parts by weight of cyclohexanone, 30 parts by weight of isobutanol, 5 parts by weight of the adduct of 7 mol of ethylene oxide to 1 mol of isooctylphenol and 5 parts by weight of the adduct of 40 mol of ethylene oxide to 1 mol of castor oil (active ingredient content 16% by weight).

V. 80 parts by weight of a compound according to the invention are mixed thoroughly with 3 parts by weight of sodium diisobutylnaphthalene-alpha-sulfonate, 10 parts by weight of sodium lignosulfonate from a sulfite waste liquor and 7 parts by weight of pulverulent silica gel, and the mixture is ground in a hammer mill (active ingredient content 80% by weight).

VI. 90 parts by weight of a compound according to the invention are mixed with 10 parts by weight of N-methyl-α-pyrrolidone, which gives a solution which is suitable for use in the form of microdrops (active ingredient content 90% by weight).

VII. 20 parts by weight of a compound according to the invention are dissolved in a mixture composed of 40 parts by weight of cyclohexanone, 30 parts by weight of isobutanol, 20 parts by weight of the adduct of 7 mol of ethylene oxide to 1 mol of isooctylphenol and 10 parts by weight of the adduct of 40 mol of ethylene oxide to 1 mol of castor oil. Pouring into, is and finely dividing the solution in, 100,000 parts by weight of water gives an aqueous dispersion comprising 0.02% by weight of the active ingredient.

VIII. 20 parts by weight of a compound according to the invention are mixed thoroughly with 3 parts by weight of sodium diisobutylnaphthalene-α-sulfonate, 17 parts by weight of sodium lignosulfonate from a sulfite waste liquor and 60 parts by weight of pulverulent silica gel, and the mixture is ground in a hammer mill. Finely distributing the mixture in 20,000 parts by weight of water gives a spray mixture comprising 0.1% by weight of the active ingredient.

Granules, eg. coated granules, impregnated granules and homogeneous granules, can be prepared by binding the active ingredients to solid carriers. Examples of solid carriers are mineral earths, such as silica gel, silicic acids, silica gels, silicates, talc, kaolin, attaclay, limestone, lime, chalk, bole, loess, clay, dolomite, diatomaceous earth, calcium sulfate magnesium sulfate, magensium oxide, ground synthetic substances, fertilizers, eg. ammonium sulfate, ammonium phosphate, ammonium nitrate, ureas, and products of vegetable origin, such as cereal meal, tree bark meal, wood meal and nutshell meal, cellulose powders and other solid carriers.

Various types of oils, or herbicides, fungicides, other pesticides, or bactericides, may be added to the active ingredients, if desired only immediately prior to use (tank mix). These agents can be admixed to the compositions according to the invention in a ratio by weight of from 1:10 to 10:1.

SYNTHESIS EXAMPLES

The protocols given in the synthesis examples below were used for obtaining other compounds I by altering the starting compounds appropriately. The resulting compounds are listed in the tables below together with physical data.

Example 1

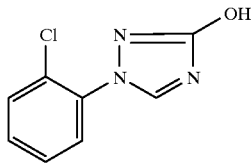

29 g of potassium cyanate in 100 ml of water are added dropwise to 50 g of 2-chlorophenylhydrazine hydrochloride in 200 ml of water. The mixture is subsequently stirred overnight at room temperature, and the crystals which have precipitated are filtered off with suction, washed with water and dried. This gives 49.32 g (m.p. 178.7° C.), which are treated with 100 ml of triethyl orthoformate without further purification. The mixture is subsequently stirred at 120° C., and the ethanol formed in this process is distilled off. The product which has precipitated is filtered off with suction, washed using methylene chloride and once using methyl tert-butyl ether, and dried. This gives 33.7 g of product in the form of colorless crystals which are employed in Example 2 without further purification.

Example 2

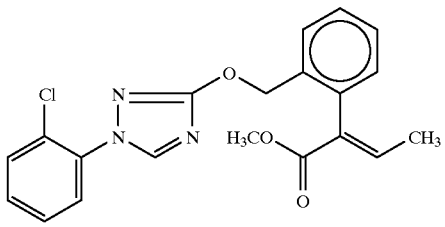

25.4 g of 3-hydroxy-[2-chlorophenyl)triazole from Example 1 are dissolved in 900 ml of DMF, and the solution is treated with 62.9 g of potassium carbonate. Then, 100 mg of potassium iodide are added, and a solution of 35 g of methyl α-[-bromomethylphenyl)-β-methylacrylate in 500 ml of DMF is added dropwise at room temperature. The mixture is stirred for 5 hours at 45° C. and the product is precipitated by adding ice-water. It is then taken up in ethyl acetate, washed with ater, dried over sodium sulfate and concentrated. 46.3 g of product are obtained as a viscous oil.
$^1$H NMR(CDCl$_3$): δ=8.7–7.1 (m,8H) S,2 (S,2H), 3.7 (S,3H), 1.65 (d, 3H).

Example 3

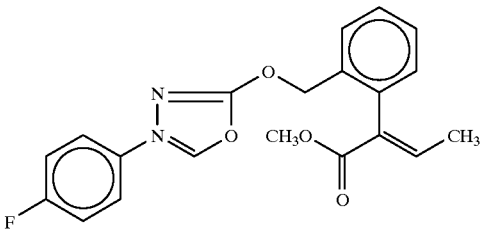

1 g of 5-hydroxy-3-(4-fluorophenyl)oxadiazole is refluxed for 10 hours together with 50 ml of n-hexane, 1.5 g of silver carbonate and 1.5 g of methyl α-(2-bromomethylphenyl)-β-methylacrylate. Then, another 1 g of silver carbonate and 50 ml n-hexane are added and the mixture is refluxed for a further 10 hours. For working-up, the mixture is filtered, the filtrate is washed using n-hexane, and the n-hexane phase is washed with water, dried over sodium sulfate and concentrated. This gives 0.7 g of product which can be further purified by chromatography over silica gel using ethyl acetate/n-heptane (1:1).
$^1$H NMR(CDCl$_3$): δ=8.0 (m, 2H), 7.6 (m,1H), 7.5–7.1 (m,5H), 5.4 (S,2H), 3.7 (S,3H) and 1.65 (d,3H).

TABLE

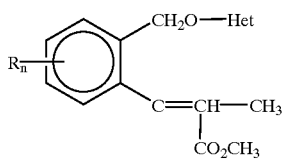

| No. | R$^n$ | Het | M.p. (C° [sic]); IR(cm$^{-1}$); NMR(ppm) |
|---|---|---|---|
| 1 | H | N-(2,4-Cl$_2$-phenyl)-1,2,4-triazol-3-yl | 1713, 1544, 1328, 1255, 1036 |
| 2 | H | N-(2-Cl-phenyl)-1,2,4-triazol-3-yl | 1714, 1543, 1329, 1255, 1038 |
| 3 | H | N-(3-Cl-phenyl)-1,2,4-triazol-3-yl | 1713, 1544, 1328, 1255, 766 |
| 4 | H | N-(4-Cl-phenyl)-1,2,4-triazol-3-yl | 104–106 |
| 5 | H | N-(2-CH$_3$-phenyl)-1,2,4-triazol-3-yl | 1713, 1540, 1328, 1255, 1037 |
| 6 | H | N-(3-CH$_3$-phenyl)-1,2,4-triazol-3-yl | 1713, 1542, 1328, 1255, 748 |
| 7 | H | N-(3,5-Cl$_2$-phenyl)-1,2,4-triazol-3-yl | 1708, 1556, 1330, 1261, 768, 748 |

TABLE-continued

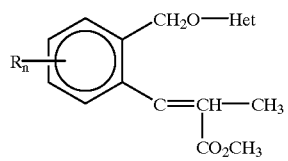

| No. | $R^n$ | Het | M.p. (C° [sic]); IR(cm$^{-1}$); NMR(ppm) |
|---|---|---|---|
| 8 | H | N-(3,4-Cl$_2$-phenyltriazol-3-yl | 1698, 1549, 1268, 991, 816 |
| 9 | 3-Cl | N-(5-CF$_3$-2-pyridyl)-1,2,4-triazol-3-yl | 119–121 |
| 10 | H | N-phenyl-1,2,4-triazol-3-yl | 1714, 1543, 1327, 1255, 759 |
| 11 | H | N-(4-CH$_3$-phenyl)-1,2,4-triazol-3-yl | 80 |
| 12 | H | N-(2-pyridyl)-1,2,4-triazol-3-yl | 1715, 1543, 1455, 1323, 1256 |
| 13 | H | N-(4-F-phenyl)-1,2,4-triazol-3-yl | 116 |
| 14 | H | N-(2,3-Cl$_2$-phenyl)-1,2,4-triazol3-yl [sic] | 1713, 1544, 1328, 1255, 765 |
| 15 | H | N-(4-CF$_3$-phenyl)-1,2,4-triazol-3-yl | 1713, 1548, 1319, 1256, 1067 |
| 16 | H | N-(4-tert-butylphenyl)-1,2,4-triazol-3-yl | 1714, 1543, 1328, 1038 |
| 17 | H | N-(4-tert-butoxyphenyl)-1,2,4-triazol-3-yl | 1713, 1546, 1258, 1163, 1038 |
| 18 | H | N-(5-CF$_3$-2-pyridyl)-1,2,4-triazol-3-yl | 1713, 1548, 1318, 1263, 1131 |
| 19 | H | N-(5-Cl-2-pyridyl)-1,2,4-triazol-3-yl | 1713, 1543, 1470, 1324, 1253 |
| 20 | H | 3-phenyloxa-2,4-diazol-5-yl | 1717, 1601, 1363, 1254, 751 |
| 21 | H | 2-(4-Cl-phenyl)oxa-3,4-diazol-5-yl | 96–98 |
| 22 | H | 3-(4-F-phenyl)oxa-2,4-diazol-5-yl | 1717, 1593, 1419, 1255, 765 |
| 23 | H | 3-(4-Cl-phenyl)oxa-2,4-diazol-5-yl | 1717, 1598, 1412, 1361, 763 |
| 24 | H | N-(2-CH$_3$, 4-Cl-phenyl)-1,2,4-triazol-3-yl | 47 |
| 25 | H | N-(4-CH(CH$_3$)$_2$-phenyl)-1,2,4-triazol-3-yl | 1715, 1543, 1327, 1254, 1038, 748 | a: M.p. (°C.), $^1$H NMR (ppm), IR (cm$^{-1}$)

Examples for the action against fungal pests

The fungicidal action of the compounds of the general formula I was demonstrated by the following experiments:

The active ingredients were prepared as a 20% strength emulsion in a mixture of 70% by weight of cyclohexanone, 20% by weight of Nekanil® LN (Lutensol® AP6, wetting agent having emulsifying and dispersing action, based on ethoxylated alkylphenols) and 10% by weight of Emulphor® EL (Emulan® EL, emulsifier based on ethoxylated fatty alcohols) and diluted with water to give the desired concentration.

Action against Plasmopara viticola (downy mildew of grape vine)

Grape vines in pots (variety: "MUller Thurgaunn") were sprayed with the preparation of active ingredient to run off point (rate: 16 ppm). After 8 days, the plants were sprayed with a zoospore suspension of the fungus *Plasmopara viticola* and kept for 5 days at 20–30° C. and high atmospheric humidity. Prior to assessment, the plants were subsequently kept for 16 hours at high atmospheric humidity. The plants were scored visually.

In this test, the plants which had been treated with the compounds according to the invention Nos. 1, 2, 4, 6, 7, 10, 11 and 13 showed a disease level of 10% and less, while the plants which had been treated with the known active ingredients A and B (EP-A 280 185, Example No. 124 and No. 127, respectively) showed a disease level of 40%. The disease level amongst the untreated (control) plants was 70%.

In a corresponding test, the plants which had been treated with the compounds according to the invention Nos. 14, 15, 16, 18, 22, 23, 24 and 25 showed a disease level of 15% and less, while the disease level amongst the untreated (control) plants was 70%.

Action against *Puccinia recondita* (leaf rust of wheat)

Leaves of wheat seedlings (variety "Kanzler") were dusted with spores of the leaf rust fungus (Puccinia recondita). The plants which had been treated in this manner were incubated for 24 hours at 20–22° C. and a relative atmospheric humidity of 90–95% and subsequently treated with an aqueous preparation of the active ingredient (rate: 63 ppm). The extent of fungal development was determined after a further 8 days at 20–22° C. and relative atmospheric humidity of 65–70%. The plants were assessed visually.

In this test, the plants which had been treated with the compounds according to the invention Nos. 1, 2, 4, 6 and 9 showed a disease level of 5% and less, while the plants which had been treated with the known active ingredients A bzw. B (EP-A 280 185, Example No. 124 and No. 127, respectively) showed a disease level of 60% and 25%, respectively. The disease level amongst the untreated (control) plants was 75%.

In a corresponding test, the plants which had been treated with the compounds according to the invention Nos. 15, 16, 18, 24 and 25 showed a disease level of 15% and less, while the disease level amongst the untreated (control) plants was 75%.

Examples for the action against animal pests

The action of the compounds of the general formula I against animal pests was demonstrated by the following experiments:

The active ingredients were formulated a. as a 0.1% strength solution in acetone or b. as a 10% emulsion in a mixture of 70% by weight of cyclohexanone, 20% by weight of Nekanil® LN (Lutensol® AP6, wetting agent having emulsifying and dispersing action, based on ethoxylated alkylphenols) and 10% by weight of Emulphor® EL (Emulan® EL, emulsifier based on ethoxylated fatty alcohols)

and diluted, in the case of a. with acetone and in the case of b. with water, to give the desired concentration.

After the experiments had ended, in each case the lowest concentration was determined at which the compounds still caused an 80 to 100% inhibition or mortality in comparison

We claim:

1. A compound of the formula I

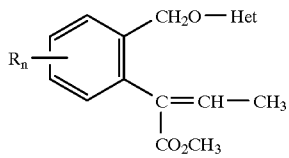

where the index and the substituents have the following meanings:

R is cyano, halogen, $C_1$–$C_4$-alkyl or $C_1$–$C_4$-alkoxy;

n is 0, 1 or 2, it being possible for the substituents R to differ from each other if n is 2;

Het is 1,2,4-triazole having attached to it an unsubstituted or substituted phenyl ring or an unsubstituted or substituted 6-membered heteroaromatic ring which, in turn, has one to four nitrogen atoms.

2. The compound of the formula I as defined in claim 1 where Het is

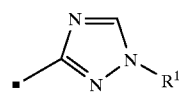

where the bond designated by ■ represents the bond to the oxygen atom wherein $R^1$ represents an unsubstituted or substituted 6-membered heteroaromatic ring which, in turn, has one to four nitrogen atoms.

3. The compound of the formula I as defined in claim 1 where Het is

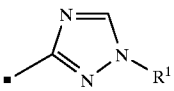

and $R^1$ has the following meanings:

phenyl or a 6-membered heteroaromatic ring which has one to three nitrogen atoms, it being possible for these radicals to be partially or fully halogenated and to have attached to them one to three of the following groups: $C_1$–$C_6$-alkyl, $C_1$–$C_6$-haloalkyl, $C_1$–$C_6$-alkoxy, $C_1$–$C_6$-haloalkoxy, $C_1$–$C_6$-alkylamino, di-$C_1$–$C_6$-alkylamino and $C_1$–$C_6$-alkoxycarbonyl.

4. A composition which is suitable for controlling animal or fungal pests which comprises a solid or liquid carrier and a compound of the formula I as defined in claim 1.

5. A method of controlling fungal pests, which comprises treating the fungi or the materials, plants, soil or seed to be protected against fungal infection with an effective amount of a compound of the formula I as defined in claim 1.

6. A method of controlling animal pests, which comprises treating the animal pests or the materials, plants, soil or seed to be protected against them with an effective amount of a compound of the formula I as defined in claim 1.

7. A process for the preparation of a compound of the formula I as defined in claim 1, which comprises reacting a compound of the formula II HO—Het with a benzyl compound of the formula III

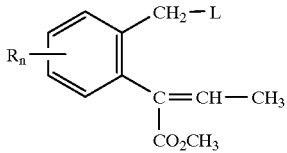

where L is a nucleophilically exchangeable leaving group, in an inert organic solvent in the presence of a base.

* * * * *